(12) United States Patent
Cannon et al.

(10) Patent No.: US 10,327,811 B2
(45) Date of Patent: Jun. 25, 2019

(54) TRANSSEPTAL CROSSING NEEDLE DEVICE

(71) Applicant: Creganna Unlimited Company, Galway (IE)

(72) Inventors: William Cannon, Galway (IE); Brendan Marrinan, Galway (IE); Liam Farrissey, Galway (IE); Bernard McDermott, Mayo (IE); Richard Gribbons, Galway (IE)

(73) Assignee: Creganna Unlimited Company, Galway (IE)

( * ) Notice: Subject to any disclaimer, the term of this patent is extended or adjusted under 35 U.S.C. 154(b) by 275 days.

(21) Appl. No.: 15/030,437

(22) PCT Filed: Oct. 24, 2014

(86) PCT No.: PCT/US2014/062252
§ 371 (c)(1),
(2) Date: Apr. 19, 2016

(87) PCT Pub. No.: WO2015/061734
PCT Pub. Date: Apr. 30, 2015

(65) Prior Publication Data
US 2016/0242813 A1    Aug. 25, 2016

Related U.S. Application Data

(60) Provisional application No. 61/895,579, filed on Oct. 25, 2013.

(51) Int. Cl.
*A61B 17/00* (2006.01)
*A61B 17/34* (2006.01)
(Continued)

(52) U.S. Cl.
CPC ...... *A61B 17/3478* (2013.01); *A61B 17/3403* (2013.01); *A61B 2017/00247* (2013.01);
(Continued)

(58) Field of Classification Search
CPC .......... A61M 25/06; A61M 2025/0089; A61M 2025/0687; A61M 25/0084;
(Continued)

(56) References Cited

U.S. PATENT DOCUMENTS 5,785,689 A      7/1998  de Toledo et al.
6,053,904 A *    4/2000  Scribner ........... A61M 25/0017
                                                  604/104

(Continued)

FOREIGN PATENT DOCUMENTS

EP        0995453 A1    4/2000

*Primary Examiner* — Martin T Ton
(74) *Attorney, Agent, or Firm* — Schiff Hardin LLP

(57) ABSTRACT

In a transseptal crossing needle device for inserting an outer sheath through a septum, an inner dilator sheath is received within the outer sheath and a needle having a curved end portion adjacent a tip of a tip portion of the needle is provided, the needle being received in the inner dilator sheath. The needle tip portion comprises an angled transverse end surface terminating at said tip and slanting away from an inner concave curved wall of said inner sheath curved by the needle curved end portion, the needle tip being spaced not only away from said inner concave curved wall of said inner sheath but also away from an inner convex curved wall of said inner sheath opposite said concave wall to reduce or eliminate skiving of material from the concave and convex inner walls of the inner sheath.

9 Claims, 4 Drawing Sheets

(51) Int. Cl.
*A61M 25/00* (2006.01)
*A61M 25/01* (2006.01)
*A61M 25/06* (2006.01)
*A61B 90/00* (2016.01)
*A61M 29/00* (2006.01)

(52) U.S. Cl.
CPC .............. *A61B 2017/00336* (2013.01); *A61B 2017/3413* (2013.01); *A61B 2090/062* (2016.02); *A61B 2090/0811* (2016.02); *A61B 2090/3925* (2016.02); *A61B 2090/3966* (2016.02); *A61M 25/0041* (2013.01); *A61M 25/0152* (2013.01); *A61M 25/06* (2013.01); *A61M 29/00* (2013.01); *A61M 2025/0089* (2013.01); *A61M 2025/0681* (2013.01)

(58) Field of Classification Search
CPC .......... A61M 25/0095; A61M 25/0612; A61M 25/065; A61B 17/3403; A61B 17/0478; A61B 2017/00247; A61B 18/1447; A61B 2018/1425; A61B 2018/1427; A61B 2018/1432

USPC ........................................................ 606/185
See application file for complete search history.

(56) References Cited

U.S. PATENT DOCUMENTS

| | | |
|---|---|---|
| 2003/0073902 A1 | 4/2003 | Hauschild et al. |
| 2005/0149097 A1* | 7/2005 | Regnell ............ A61M 25/0068 606/191 |
| 2005/0267490 A1 | 12/2005 | Secrest et al. |
| 2006/0064062 A1 | 3/2006 | Gurusamy et al. |
| 2007/0005019 A1 | 1/2007 | Okishige |
| 2007/0156164 A1* | 7/2007 | Cole ................. A61B 17/32053 606/187 |
| 2009/0171276 A1* | 7/2009 | Bednarek .......... A61B 17/00234 604/96.01 |
| 2010/0160731 A1 | 6/2010 | Giovannini et al. |
| 2012/0265156 A1* | 10/2012 | Devereux ................ A61M 5/46 604/263 |
| 2012/0289987 A1 | 11/2012 | Wilson et al. |
| 2013/0190609 A1 | 7/2013 | Fischer, Jr. |
| 2015/0032142 A1* | 1/2015 | Silvestro ............ A61B 17/3415 606/185 |

* cited by examiner

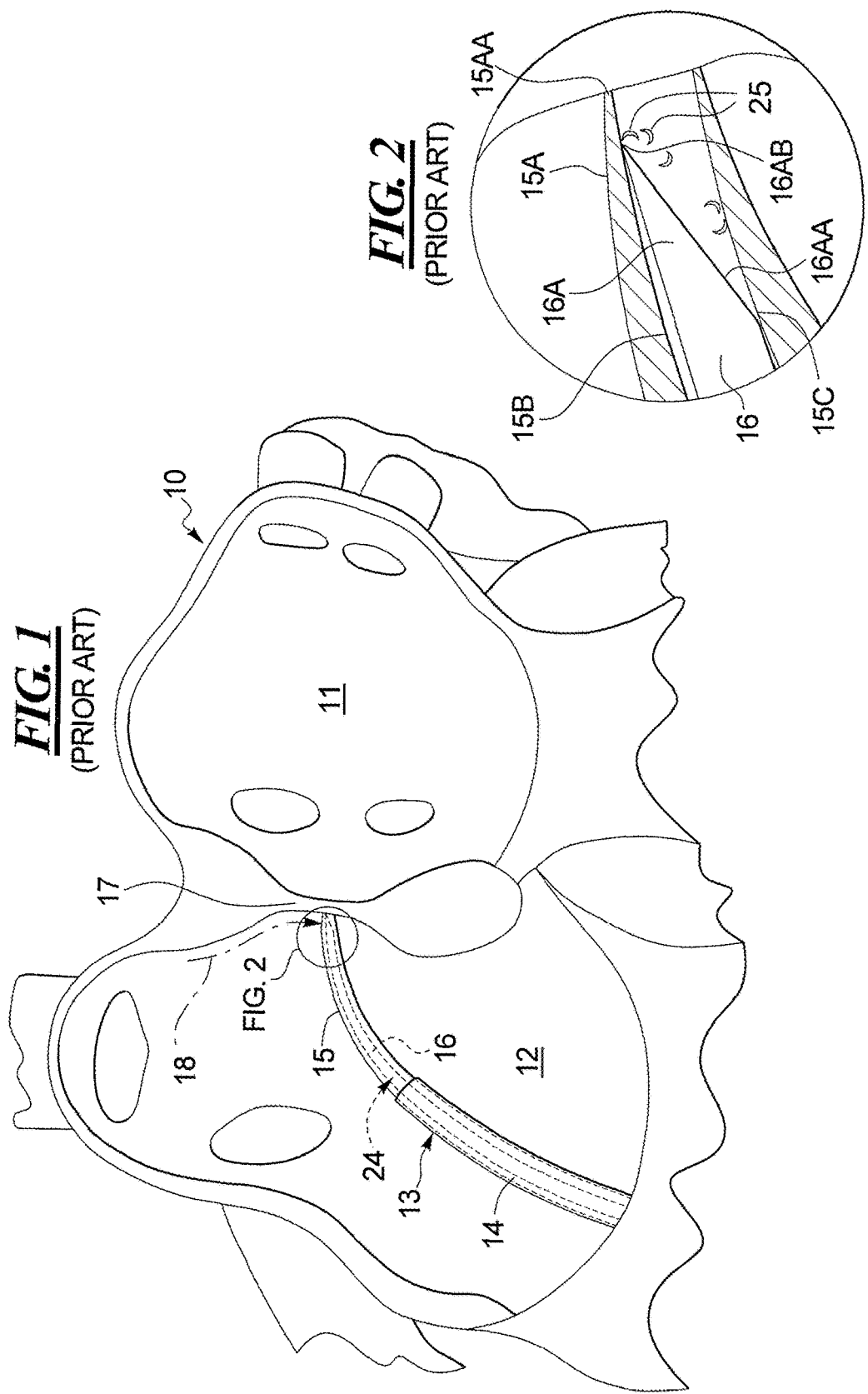

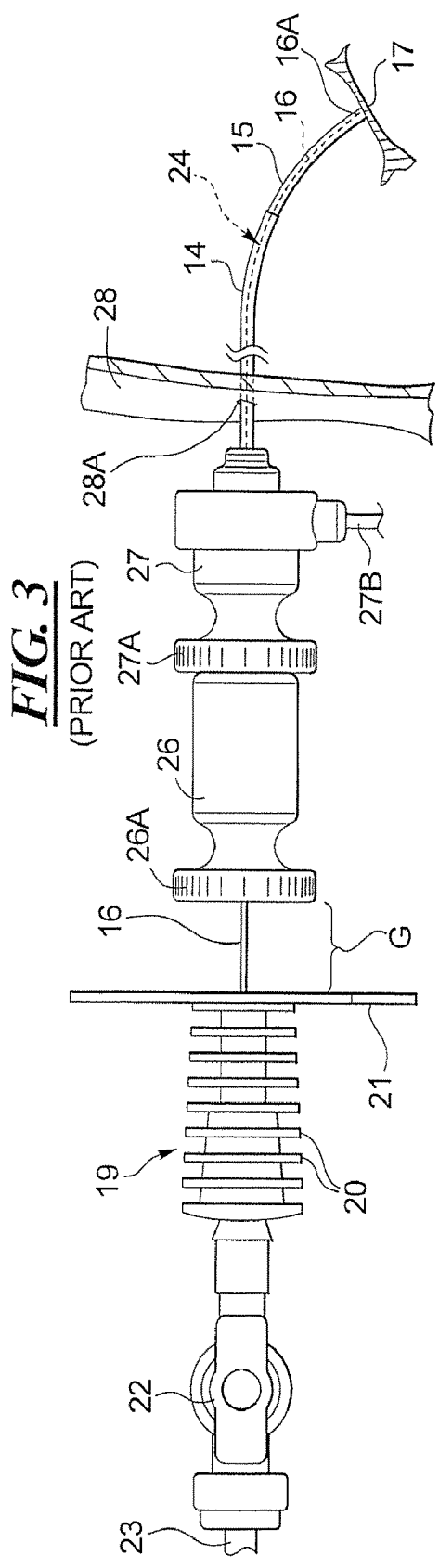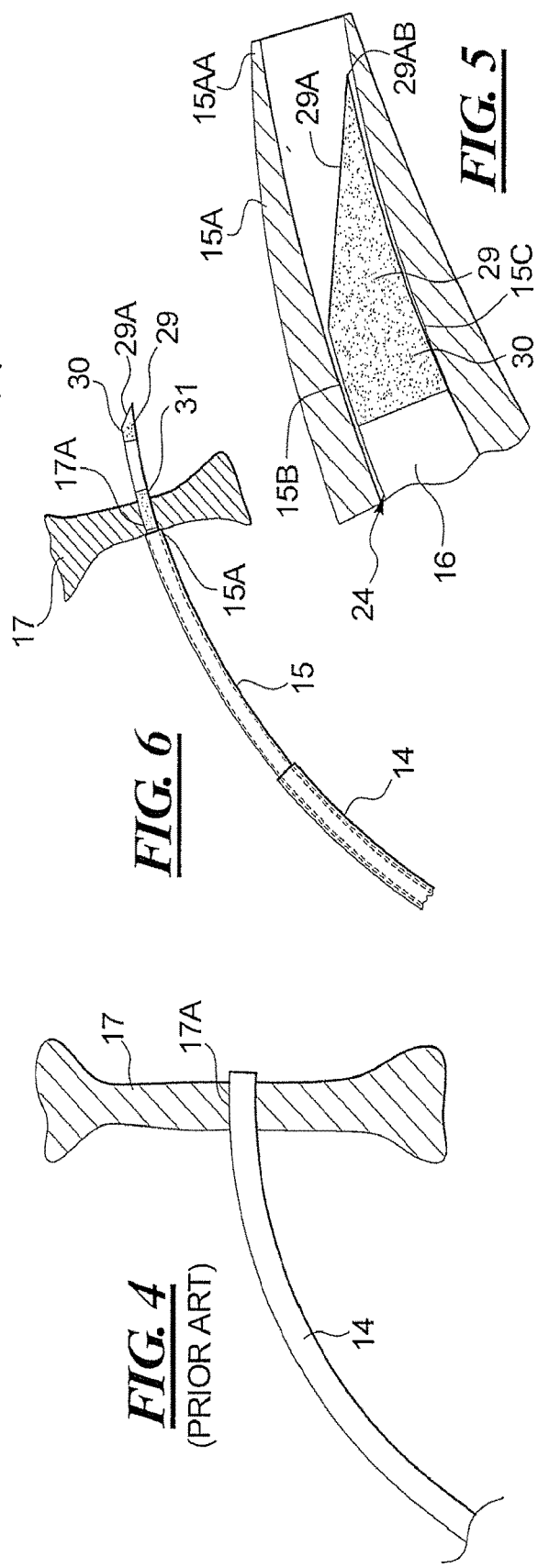

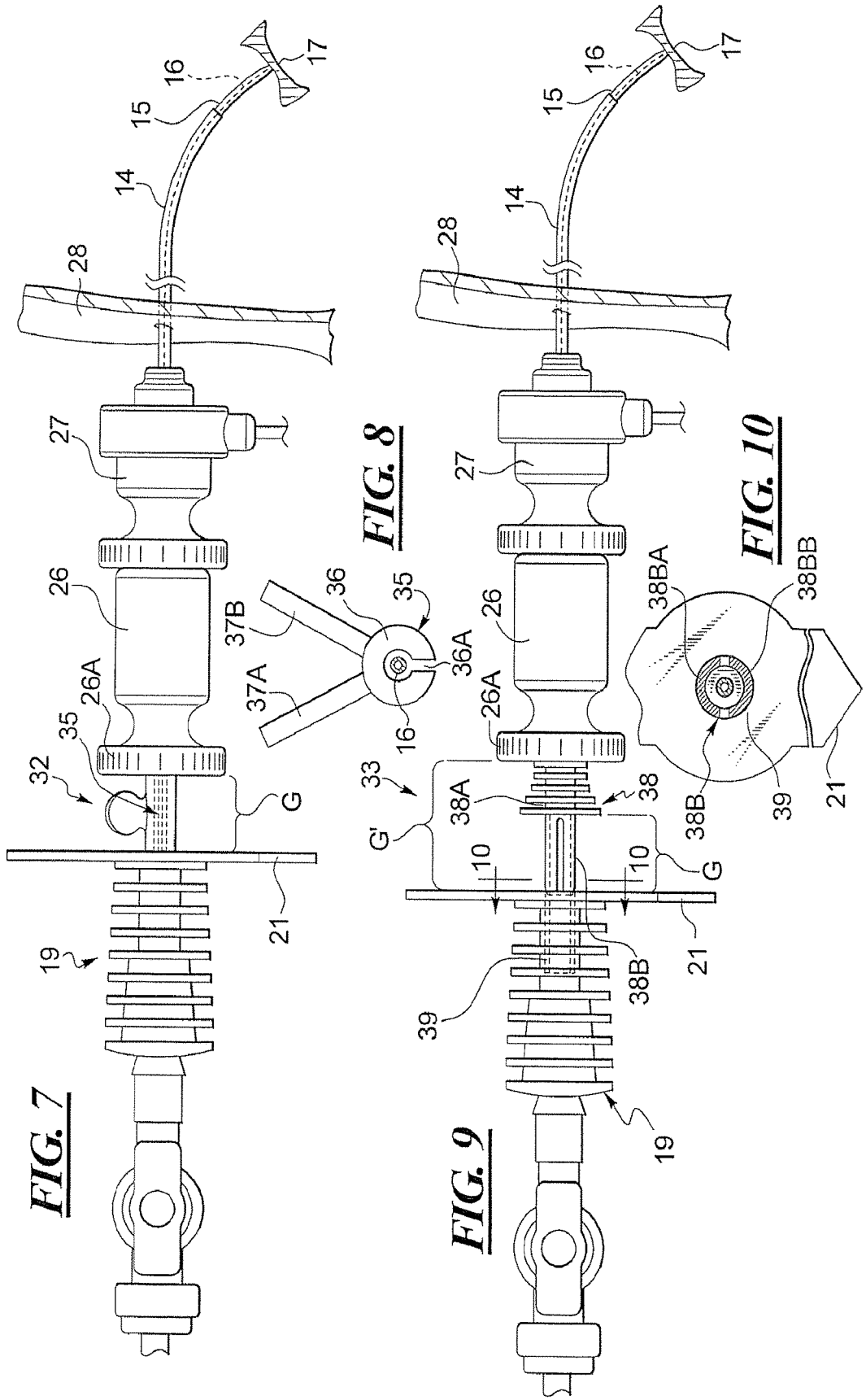

TRANSSEPTAL CROSSING NEEDLE DEVICE

CROSS-REFERENCE TO RELATED APPLICATION

This national stage entry from the PCT application claims the benefit of U.S. Provisional Patent Application Ser. No. 61/895,579, filed Oct. 25, 2013, which is incorporated herein by reference.

BACKGROUND

Transseptal crossing, puncture, or catheterization is a means of gaining access to the left atrium 11 from the right atrium 12 of the heart 10. These chambers of the heart are shown in prior art FIG. 1 but since the patient is being viewed from the front, the left atrium 11 is shown on the right side and the right atrium 12 is shown on the left side in the drawing figure. This transseptal crossing, puncture, or catheterization was first described independently by Ross and Cope in 1959, as discussed in the article "Transseptal Catheterization in 2010: Crossing into a New Decade", EP Lab Digest, February 2010. In FIG. 1 one may observe a transseptal crossing needle device 13 having an outer sheath 14, an inner dilator sheath 15, and a hollow needle 16 positioned within the inner sheath 15. The needle 16 has a curved portion 24 progressing towards a tip portion 16A. The inner sheath 15, as most clearly shown in expanded prior art view FIG. 2, has a partial conical tip tapering portion 15A and also is curved near its end by the forces exerted by the needle curved portion 24. The hollow needle 16 has a transverse cut tip portion 16A terminating in a tip 16AB at the end of upwardly sloping transverse end surface 16AA. Note that this surface 16AA slopes towards an upper concave curved inner wall 15B of the end portion of the inner sheath 15 and away from a lower convex curved inner wall 15C. Over the past 10 years or so, the number of transseptal crossings being performed has increased dramatically, driven mostly by the increase in atrial fibrillation (AF) ablation procedures within electrophysiology. This remains the predominant use of transseptal crossing devices. However, new minimally invasive percutaneous procedures related to structural heart are also being developed that use these devices. These procedures include the closure of atrial septal defects, left atrial appendage closure device implementation, and left ventricular assist device implantation.

Transseptal crossing across what is known as the septum 17 (fossa ovalis) as shown in FIG. 1 to gain access to the left atrium 11 is acknowledged as a critical and very dangerous part of all of the above procedures. Clinical guidelines support the use of multiple visualization checks when conducting this procedure with many physicians using a combination of fluoroscopy, echocardiography, pacing, and contrast injection, along with their own judgment and experience. For a number of different procedures, access to the left atrium 11 via the septum 17 (fossa ovalis) as described above is required. These procedures include mitral valve repair, mitral valvoplasty, atrial fibrillation ablation, and closure of left atrial appendage repair or closure.

Referring to FIG. 1, according to the prior art procedure the tapered conical end portion 15A of the inner dilator sheath 15, and more particularly the leading end 15AA, is moved down the septum 17 as shown by the arrow 18 until it reaches the relatively thinnest part of the septum 17. Thereafter the hollow needle 16 is pushed beyond the inner sheath end 15AA and penetrates through the septum 17. Thereafter the inner sheath 15 functioning as a dilator dilates with its conical end portion 15A the opening provided by the needle and pushes through, thus dilated the needle opening. Thereafter the outer sheath 14 is pushed along the inner sheath 15 through the dilated opening 17A. As shown in FIG. 4, the needle 16 and inner dilator sheath 15 are then withdrawn, leaving only the outer sheath 14 in the opening 17A, which is then available for use with medical instrumentation to be inserted into the left atrium 11 as described above.

The tip portion 16A of the needle 16 penetrates the septum 17 using ultrasound visualization.

Prior art FIG. 3 illustrates how the physician manipulates the inner and outer sheaths 15 and 14, and needle 16, for the above-described procedure. Initially before introduction into the human body, the needle 16 is pushed through the inner dilator sheath 15 until the tip portion 16A with tip 16AB is positioned near the tapered end portion 15A as shown in FIG. 2. A needle handle 19 firmly attached to an end of the hollow needle 16 is provided for manipulating the needle through the inner sheath 15. The needle handle 19 has a plurality of finger grip knurls 20. A leading end of the handle 19 has a pointing arrow 21 to indicate a rotational position of the needle 16, and particularly of the needle curved portion 24 leading to the tip portion 16A at the end of the hollow needle 16. The steel needle is pre-stressed into a curve at the curved portion 24 which causes a bending of the flexible inner sheath 15 and outer sheath 14 where the needle curved portion 24 is present.

Rearwardly of the finger knurls 20 is located a stop cock 22 for allowing in-flow of a liquid such as a dye introduced through a flexible hose 23 for delivery through the needle.

As illustrated in FIG. 3, the needle 16 passes through an inner dilator sheath handle 26 firmly attached to the inner dilator sheath 15. A knurled finger grip 26A is integrally formed at the needle entry end of the inner sheath handle 26 for finger gripping.

The opposite end of the inner sheath handle 26 butts against an outer sheath handle 27 having a knurled finger grip portion 27A. The outer sheath handle 27 is rigidly attached to the end of the outer sheath 14 for manipulation thereof. A hose 27B allows introduction of a fluid such as saline solution into the outer sheath 14 which surrounds the inner sheath 15.

The outer sheath 14 with the inner sheath 15 and needle 16 enter an outer wall of the human body 28 as shown at 28A and then are fed up to the heart through an artery, for example, and then to the septum 17 within the heart as explained in connection with FIG. 1 so as to create the desired diluted aperture 17A in the septum 17 as described above.

After the conical portion 15A of the inner dilator sheath 15 has been located as described above at the septum 17 in FIG. 1, then the physician pushes on the needle handle 19 to close the gap G between the leading end at arrow 21 of the handle 19 and the back surface of the inner sheath dilator handle 26. This causes the tip 16A of the needle to push out through the end 15AA of the inner sheath 15A to penetrate through the septum 17 such that thereafter a small portion of the needle at its tip portion now lies on the opposite side of the septum within the left ventricle 11.

During introduction and movement of the tip portion 16A having the transverse upwardly slanting angled end surface 16AA as shown in FIG. 2 to form the tip 16AB, shavings 25 can be scraped off by skiving at the upper concave curved inner wall 15B of the inner sheath 15 by the tip 16AB running along this concave curved inner wall 15B. This is undesirable and a disadvantage of this prior art device.

Another disadvantage of the prior art system is that presently the skill of the operator and "feel" are critical determining factors in the successful placement of the needle 16 and crossing of the fossa 17. Significant training is required in order for a physician to complete this procedure correctly.

SUMMARY

It is an objective to eliminate the creation of shavings by the above-described skimming and also to provide improved safety and ease of delivery of the needle of the transseptal crossing needle device for penetration of the septum as described above.

In a transseptal crossing needle device for inserting an outer sheath through a septum, an inner dilator sheath is received within the outer sheath and a needle having a curved end portion adjacent a tip of a tip portion of the needle is provided, the needle being received in the inner dilator sheath. The needle tip portion comprises an angled transverse end surface terminating at said tip and slanting away from an inner concave curved wall of said inner sheath curved by the needle curved end portion, the needle tip being spaced not only away from said inner concave curved wall of said inner sheath but also away from an inner convex curved wall of said inner sheath concave wall to reduce or eliminate skiving of material from the concave and convex inner walls of the inner sheath.

BRIEF DESCRIPTION OF THE DRAWINGS

FIG. 1 is a cross-sectional side view of a heart with a prior art transseptal crossing needle device having a needle for puncturing through the septum of the heart;

FIG. 2 is a cross-section enlargement of the prior art device of FIG. 1 at an end of an inner sheath touching against the septum and with a needle having a needle tip positioned slightly rearwardly of the end of the inner sheath;

FIG. 3 is a side view of the prior art transseptal crossing needle device, a portion of which is shown in FIG. 1;

FIG. 4 is a cross-sectional side view of the septum with the prior art outer sheath of the transseptal device crossing through the septum;

FIG. 5 is a side cross-sectional view of an exemplary embodiment according to the invention of an improved needle tip portion;

FIG. 6 is a side view of the improved needle tip after it has passed through the septum and also showing first and second echogenic markers for ultrasound visualization at and near the improved tip;

FIG. 7 is a side view of the improved transseptal crossing needle device having not only the improved tip and markers shown in FIGS. 5 and 6, but also having a first embodiment of a spacing device between the needle handle and the inner sheath handle in a gap G also shown in prior art FIG. 3;

FIG. 8 shows an end view of the prior art spacer device of FIG. 7;

FIG. 9 shows a second embodiment of a spacer device between the needle handle and the inner sheath handle located in a bigger gap G' than the gap G shown in prior art FIG. 3;

FIG. 10 is an end view of the second embodiment of the spacer device shown in FIG. 9 looking toward the needle handle;

DESCRIPTION OF EXEMPLARY EMBODIMENTS

Figure 11:
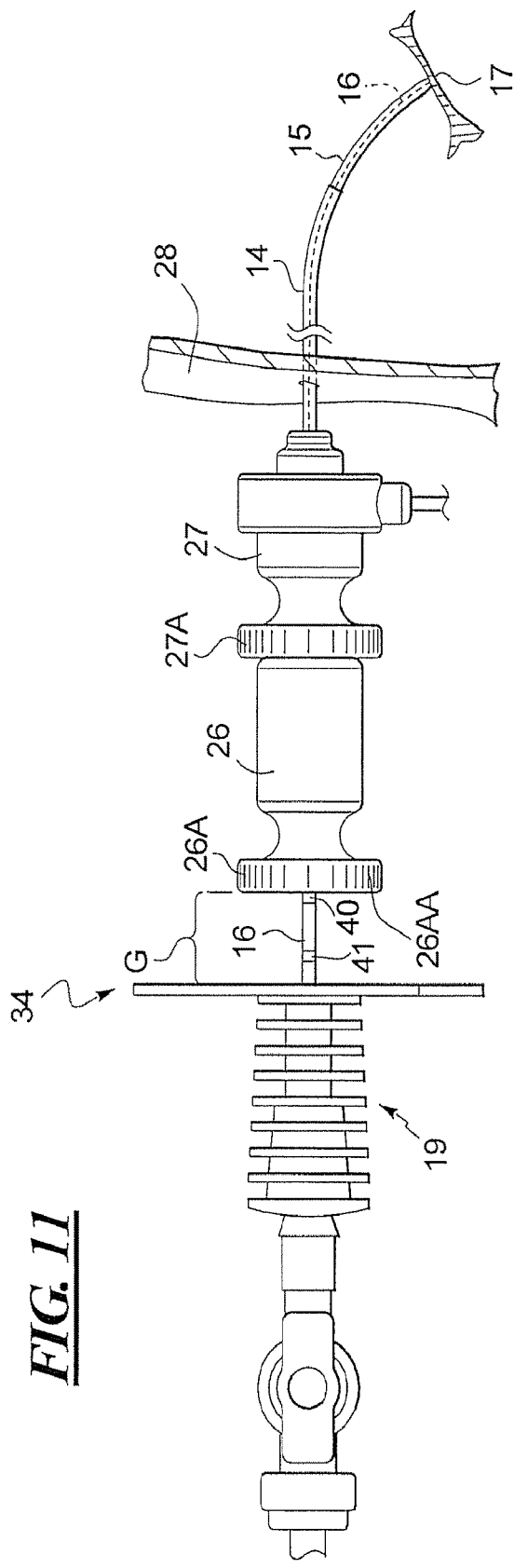
FIG. 11 is a third embodiment having first and second visible markers located in the gap G shown in prior art FIG. 3.

For the purposes of promoting an understanding of the principles of the invention, reference will now be made to the preferred exemplary embodiments/best mode illustrated in the drawings and specific language will be used to describe the same. It will nevertheless be understood that no limitation of the scope of the invention is thereby intended, and such alterations and further modifications in the illustrated embodiments and such further applications of the principles of the invention as illustrated as would normally occur to one skilled in the art to which the invention relates are included herein.

An exemplary embodiment is shown in FIG. 5 of an improved needle tip portion 29 for the improved transseptal crossing devices 32 show in FIG. 7, 33 shown in FIGS. 9, and 34 shown in FIG. 11. Hereinafter, when describing the improvements in FIGS. 5-12 of the improved transseptal needle device embodiments, components which are unchanged relative to the prior art transseptal needle device shown in FIG. 3 have retained the same reference numerals as in FIG. 3.

As shown in FIG. 5, the improved tip portion 29 has its transverse end surface 29A downwardly sloping towards the convex curved inner wall 15C of sheath 15 as it proceeds to the tip 29AB. This slope is opposite to the slope of the prior art tip portion 16A which slopes upwardly towards the concave inner wall 15B of the sheath. This eliminates the shavings 25 caused by skiving since the leading tip 29AB does not contact the bottom convex curved inner wall 15C nor the upper concave curved inner wall 15B of the inner sheath 15. Thus skiving is prevented at the curved portion 24 of the needle and inner and outer sheaths.

As shown in FIG. 6, the needle 16 has penetrated through the septum 17 with the improved needle tip portion 29 but the inner dilator sheath 15 has its leading end 15A still abutting against the septum 17 prior to dilating at the opening by being pushed therethrough. In this figure one can see first and second echogenic markers 30 and 31 which allow the physician to visualize by ultrasound a location of the tip 29AB at improved tip portion 29 and also the amount of the needle 16 which has been pushed and penetrated through the septum 17 by use of the marker 31 just beginning to emerge from the hole 17A in the septum 17. The first echogenic marker 30 is also shown in FIG. 5. These echogenic markers 30 and 31 are also shown in enlarged view in FIG. 12 along with the improved tip portion 29.

In this improvement using the echogenic markers 30 and 31, visualization of the needle is aided using echo ultrasound. In the prior art the needle and needle tip are very difficult to see under trans-esophageal echo (TEE) or trans thoracic echo (TTE) with only the very tip of the needle being sometimes visible. With the improvement of the present exemplary embodiment with the markers 30 and 31, visualization is improved since the marker 30 at the tip of the needle can be seen after it crosses through the septum 14. This prevents advancement of the needle too far which could possibly damage a back wall of the left atrium 11 and inadvertently puncture that wall opposite the septum. Also the markers 30 and 31 provide visualization of how much of the needle has penetrated through the septum.

Figure 12:
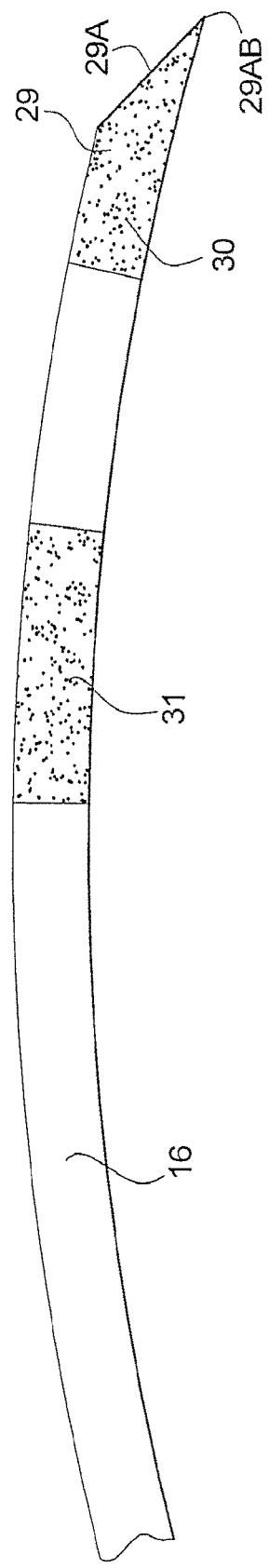
FIG. 12 shows the first and second echogenic markers previously described in connection with FIG. 6 but in an enlarged view.

The first echogenic marker 30 at the improved tip portion 29 can have a length of approximately 1-2 mm. The second echogenic marker 31 can extend for 1-5 mm, for example, and can be located between 5-30 mm from the needle tip 29AB as shown in FIGS. 6 and 12. As explained above, the second marker 31 can be used for additional visualization during delivery of the needle. Also it is noted these markers 30 and 31 are useful for the user since the echo ultrasound is a 2D medium whereas the device is used in 3D space. This can translate and be used into characterizing the angulation of the improved needle tip portion 29.

The visualization for the echogenic markers 30 and 31 is achieved by a surface texturing which can be accomplished in a number of ways including sand or grit blasting, laser ablation of the metal surface, grinding or mechanically modifying the outer surface of the needle.

With respect to the previously described improved tip portion 29 the transverse end surface 29A is achieved by cutting or grinding a metal hypo tube of which the needle is constructed (for example stainless steel, cobalt, chrome alloy, nitinol). This angled tip portion is created by grinding, for example, at the distal end. As previously described, the angled tip portion minimizes skiving (cutting off of thin layers of the material from the convex 15C or concave 15B curved inside walls of the dilator inner sheath 15 during insertion of the needle). This plastic material, if dislodged, could enter the vascular system and cause a blockage.

A further improvement will now be described with respect to the improved transseptal needle device 32 shown in FIG. 7 according to a first embodiment. Here a first embodiment spacer device is shown at 35 and in an end view in FIG. 8. This spacer device 35 comprises a springly metal or plastic clip having a split tubular section 36 split at 36A with clip ears 37A and 37B which are pressed together by the user's fingers to open the springy clip for placement around the hollow needle 16 in the gap G previously described in prior art FIG. 3. This insures that the needle tip 29AB as shown in FIG. 5 remains just inside the end 15AA of the inner sheath 15 prior to insertion through the septum. Thereafter when the physician is ready to push the needle tip 29AB through the septum 17, the user removes the spacer 35 and the user then closes the gap G by pushing on the needle handle 19 until the arrow portion 21 butts up against the knurled portion 26A of handle 26 of the inner dilator sheath 15, at which time a further protrusion of the needle tip through the septum as illustrated in FIG. 6 is prevented. This improvement can be explained as follows. Traditionally the physician must use X-ray to try and visualize the needle inside the dilator sheath or estimate a distance from a tip of the needle to a tip or end of the conical portion of the inner dilator sheath by looking at the gap G between the needle handle 19 and the inner dilator sheath handle 26 as illustrated in prior art FIG. 3. A second embodiment spacer device 38 in an improved transseptal needle device 33, is shown in FIGS. 9 and 10. This spacer device 38 has a handle portion 38A and a split collar section 38B received by friction fit in a circular slot 39 in an improvement to the prior art handle 19. In this embodiment a gap G' greater than the gap G is provided wherein the physician or user sets the insertion distance of the split collar section 38B to same gap G described above in connection with prior art FIG. 3. Then when the user pushes on the handle 19 the gap G is closed off so that a new gap G'-G results due to the longitudinal extent of the handle portion 38A. This also achieves safe positioning of the needle tip as previously described.

FIG. 10 shows an end view looking towards the pointer 21 of the handle 19 and illustrates the collar sloped circular slot 39 for receiving the two split collar sections 38BA and 38BB of the split collar 38B.

FIG. 11 shows a further improved transseptal crossing device 34 according to a third embodiment for spacing and which is used instead of the spacer devices 35 shown in FIGS. 7 and 38 in FIG. 9. Here first and second visual markers 40 and 41 are provided located in gap G in prior art FIG. 3. These visual markers 40 and 41 on the needle 16 are, for example, printed on the needle 16 shaft as shown in FIG. 11. The first marker 40 is used relative to the end surface 26AA of the knurled portion 26A of the dilator inner sheath handle 26. This first marker 40 identifies when the tip 29AB of the needle is approximately 2-3 cm from the opening at the end 15AA of the inner dilator sheath 15. The second visual marker 41 indicates when the tip 29AB is about to exit the distal end of the dilator inner sheath 15 such as shown in FIG. 5. These first and second visual markers 40 and 41 external to the body surface 28 allow physicians to accurately position the needle tip 29AB for delivery without the risk of it being exposed during delivery.

The first and second markers 40 and 41 can be printed using luminous ink to make them highly visible in dimly lit catheterization labs. These visual markers 40 and 41 are particularly effective for inexperienced users as they become familiar with the procedure and the equipment.

Although preferred exemplary embodiments are shown and described in detail in the drawings and in the preceding specification, they should be viewed as purely exemplary and not as limiting the invention. It is noted that only preferred exemplary embodiments are shown and described, and all variations and modifications that presently or in the future lie within the protective scope of the invention should be protected.

We claim as our invention:

1. A transseptal crossing needle device for inserting an outer sheath through a septum, comprising:
    an inner dilator sheath received within said outer sheath, the inner dilator sheath defining a lumen extending along a longitudinal axis of the inner dilator sheath, the inner dilator sheath having an inside wall surface at the lumen; and
    a needle received in the lumen of the inner dilator sheath, the needle being elongated and having a tip portion terminating in a tip, the elongated needle deviating from a straight line at a curved portion adjacent the tip portion of the needle, said curved portion of the needle curving a portion of the inner dilator sheath so that the longitudinal axis of the inner dilator sheath deviates from a straight line at the curved portion, the curved portion of the inner dilator sheath having a first side of the inner dilator sheath extending along an inside of a curve formed by the curved portion and an opposite side of the curved portion extending along an outside of the curve, the inside wall surface at the lumen being curved in a convex shape along the longitudinal axis at the inside of the curve to form an inner convex curved wall, and the inside wall surface at the lumen being curved in a concave shape along the longitudinal axis at the outside of the curve to form an inner concave curved wall; and
    said needle tip portion comprising an angled transverse end surface terminating at said tip and slanting away from the inner concave curved wall along the outside of the curve of said inner sheath curved by said needle curved end portion, a spacing between the angled transverse end surface and the inner concave curve wall increasing toward the tip of the needle as a result of an angle of the angled transverse end surface, said needle tip being spaced not only away from said inner concave curved wall of said inner sheath but also away from the inner convex curved wall along the inside of the curve of said inner sheath opposite said concave wall to reduce or eliminate skiving of material from both said concave and convex inner curve walls of said inner dilator sheath.

2. The device of claim 1 wherein an echogenic marker is provided at said tip portion of said needle.

3. The device of claim 2 wherein another echogenic marker spaced from said echogenic marker at said tip portion is provided on said needle spaced from said tip portion.

4. The device of claim 1 wherein a needle handle to be located outside of a body in which said septum is located is attached to an end of the needle, an outer sheath handle is connected to an end of said outer sheath, an inner sheath handle is connected to an end of said inner sheath, and a gap is defined between said needle handle and said inner sheath handle prior to said needle tip extending beyond an end of said inner sheath, and a spacer received in said gap.

5. The device of claim 4, wherein the end of the inner sheath is a first end, the inner sheath having a second end opposite the first end, wherein when said gap is narrowed or closed the needle tip protrudes beyond the second end of said inner sheath.

6. The device of claim 4 wherein said spacer comprises a clip received around a portion of said needle in said gap.

7. The device of claim 4 wherein at least one visual marker is provided in said gap on said needle between said inner sheath handle and said needle handle.

8. The device of claim 7, wherein the at least one visual marker includes two of said visual markers provided in said gap.

9. The device as claimed in claim 1, wherein the angled transverse end surface slants away from the inner concave curved wall in a direction from a proximal portion of the needle tip portion to a distal portion at the tip of the needle.

* * * * *